United States Patent
Kanbara et al.

(10) Patent No.: US 9,637,446 B2
(45) Date of Patent: May 2, 2017

(54) FLUORINE-CONTAINING NITRILE-OXIDE COMPOUND

(71) Applicants: DAIKIN INDUSTRIES, LTD., Osaka-shi, Osaka (JP); TOKYO INSTITUTE OF TECHNOLOGY, Tokyo (JP)

(72) Inventors: Tadashi Kanbara, Settsu (JP); Tsuyoshi Noguchi, Settsu (JP); Haruhiko Mouri, Settsu (JP); Toshikazu Takata, Tokyo (JP); Yasuhito Koyama, Tokyo (JP); Satoshi Uchida, Tokyo (JP); ChenGang Wang, Tokyo (JP); Cheawchan Sumitra, Tokyo (JP)

(73) Assignees: DAIKIN INDUSTRIES, LTD., Osaka (JP); TOKYO INSTITUTE OF TECHNOLOGY, Tokyo (JP)

( * ) Notice: Subject to any disclaimer, the term of this patent is extended or adjusted under 35 U.S.C. 154(b) by 0 days.

(21) Appl. No.: 14/772,908

(22) PCT Filed: Mar. 7, 2014

(86) PCT No.: PCT/JP2014/056019
§ 371 (c)(1),
(2) Date: Sep. 4, 2015

(87) PCT Pub. No.: WO2014/136952
PCT Pub. Date: Sep. 12, 2014

(65) Prior Publication Data
US 2016/0002153 A1 Jan. 7, 2016

(30) Foreign Application Priority Data
Mar. 7, 2013 (JP) .................. 2013-045759

(51) Int. Cl.
*C07C 291/06* (2006.01)
*C08F 8/30* (2006.01)

(52) U.S. Cl.
CPC .............. *C07C 291/06* (2013.01); *C08F 8/30* (2013.01)

(58) Field of Classification Search
CPC .................................................. C07C 291/06
USPC ....................................................... 528/422
See application file for complete search history.

(56) References Cited

U.S. PATENT DOCUMENTS

2011/0224380 A1  9/2011  Seo et al.

FOREIGN PATENT DOCUMENTS

| JP | 2011-208117 A | 10/2011 |
| JP | 2013-112741 A | 6/2013 |
| JP | 2013-221115 A | 10/2013 |
| PL | 106 223 B1 | 12/1979 |

OTHER PUBLICATIONS

International Search Report dated Jun. 10, 2014, issued by the International Bureau in corresponding International Application No. PCT/JP2014/056019.
International Preliminary Report on Patentability dated Sep. 8, 2015, issued by the International Bureau in corresponding International Application No. PCT/JP2014/056019.
Ekcstein et al., "Diphenylacetohydroximic Chloride Derivatives as a Synthon in 1,3-Dipolar Reactions", Polish Journal of Chemistry, 1981, vol. 55, pp. 1253-1264.
Kaminski et al., "Unusual Stability of Some Diphenylacetonitrile N—Oxide Derivatives", Polish Journal of Chemistry, 1979, vol. 53, pp. 1159-1164.
Yao et al., "Reactions of β-Nitrostyrenes with Grignard Reagents", Tetrahedron Letters, 1996, vol. 37, No. 35, pp. 6339-6342.

*Primary Examiner* — Duc Truong
(74) *Attorney, Agent, or Firm* — Sughrue Mion, PLLC

(57) ABSTRACT

A stable and easily producible compound of the formula (I):

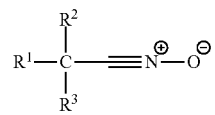

wherein $R^1$ represents a hydrocarbon group; and $R^2$ and $R^3$ represent each independently a hydrogen atom or a hydrocarbon group: provided that in at least one of $R^1$, $R^2$ and $R^3$, at least one hydrogen atoms are substituted by a fluorine atom, and each of $R^1$, $R^2$ and $R^3$ is attached via its carbon atom to a carbon atom to which a nitrileoxide group is attached.

14 Claims, No Drawings

FLUORINE-CONTAINING NITRILE-OXIDE COMPOUND

CROSS REFERENCE TO RELATED APPLICATIONS

This application is a National Stage of International Application No. PCT/JP2014/056019, filed on Mar. 7, 2014, which claims priority from Japanese Patent Application No. 2013-045759, filed on Mar. 7, 2013, the contents of all of which are incorporated herein by reference in their entirety.

TECHNICAL FIELD

The present invention relates to a multifunctional nitrile-oxide compound and a composition comprising the compound.

BACKGROUND ART

A compound having a nitrileoxide group is known to be useful as a reaction agent in various applications since it readily click-reacts with an unsaturated bond in other compound ([2+3]cycloaddition reaction). However, the nitrile-oxide compound has problems that a reaction such as dimerization readily occurs and the compound is unstable.

For this problem, it is known that a relative stable nitrileoxide compound can be obtained by modifying it into an aromatic nitrileoxide compound having substituents at ortho positions (Patent Literature 1).

PRIOR ART LITERATURE

Patent Literature

Patent Literature 4: JP 2011-208117 A

SUMMARY OF THE INVENTION

Problem to be Solved by the Invention

However, there is a case that thermal stability of the conventional aromatic nitrileoxide compounds is not sufficient in some applications. Additionally, the aromatic nitrileoxide compounds have an industrial problem when an optional substituent, in particular an alkyl group is introduced into it. For example, when a perfluoroalkyl group is introduced, a step of introducing a perfluoroalkyl group to an aromatic ring of a raw material is needed in addition to steps directly needed to synthesize a nitrileoxide compound.

Means to Solve the Problem

As a result of intensively studying of the inventors of the present invention in order to obtain a stable nitrileoxide compound having an arbitrary substituent, the inventors have found that an aliphatic nitrileoxide compound having an arbitrary substituent, for example, a perfluoroalkyl group can be obtained by reacting a nitroethylene derivative with a high nucleophilic agent (for example, a Grignard reagent, alkyllithium, or the like) to obtain a nitronate derivative and dehydrating it, and that the obtained aliphatic nitrileoxide compound has excellent stability, in particular, thermal stability.

Therefore, the present invention provides:
[1] A compound of the formula (I):

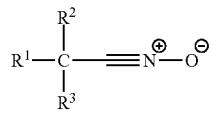

wherein
$R^1$ represents a hydrocarbon group; and
$R^2$ and $R^3$ represent each independently a hydrogen atom or a hydrocarbon group:
provided that in at least one of $R^1$, $R^2$ and $R^3$, at least one hydrogen atoms are substituted by a fluorine atom, and each of $R^1$, $R^2$ and $R^3$ is attached via its carbon atom to a carbon atom to which a nitrileoxide group is attached;

[2] The compound according to the above [1] wherein $R^1$ represents an alkyl group, an alkenyl group, an alkynyl group, a cycloalkyl group, a heterocycloalkyl group, an aryl group or a heteroaryl group which may have one or more substituents, or a group of the formula:

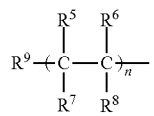

wherein:
$R^5$, $R^6$, $R^7$ and $R^8$ represent each independently a hydrogen atom, a halogen atom, an alkyl group which may be substituted by a halogen atom, or $-C(O)OR^{10}$;
$R^9$ represents a hydrogen atom, or an alkyl group which may have one or more substituents;
$R^{10}$ represents a hydrogen atom, or an alkyl group which may have one or more substituents; and
n represents an integer of 1 to 10,000; and
$R^2$ and $R^3$ are each independently a hydrogen atom, or an alkyl group, a cycloalkyl group, a heterocycloalkyl group or an aryl group which may have one or more substituents;

[3] The compound according to the above [1] or [2] wherein at least one of $R^1$, $R^2$ and $R^3$ are a perfluoroalkyl group or comprise one or more perfluoroalkyl groups;

[4] The compound according to any one of the above [1]-[3] wherein $R^1$ represents a perfluoroalkyl group, or an alkyl group substituted by one or more perfluoroalkyl groups;

[5] The compound according to any one of the above [1]-[3] wherein $R^1$ represents a group of the formula:

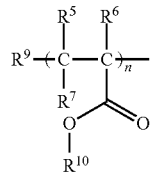

wherein:
$R^5$, $R^6$ and $R^7$ represent each independently a hydrogen atom, a halogen atom, or an alkyl group which may be substituted by a halogen atom;
$R^9$ represents a hydrogen atom, or an alkyl group which may have one or more substituents;
$R^{10}$ represents an alkyl group which may have one or more substituents; and
n represents an integer of 1 to 10,000;

[6] The compound according to any one of the above [1]-[5] which meets one or more of the following items (a)-(c);
 (a) $R^1$ is a tert-alkyl group, a sec-alkyl group, a cycloalkyl group, a heterocycloalkyl group, an aryl group or a heteroaryl group which may have one or more substituents, or a group the formula:

$$R^9-\left(\begin{array}{c}R^5\\|\\C\\|\\R^7\end{array}-\begin{array}{c}R^6\\|\\C\\|\\R^8\end{array}\right)_n-$$

wherein $R^5$, $R^6$, $R^7$, $R^8$, $R^9$ and n are as defined in the above [2];
 (b) $R^2$ is an aryl group, a tert-alkyl group or a sec-alkyl group which may be substituted by one or more substituents; and
 (c) $R^3$ is an aryl group, a tert-alkyl group or a sec-alkyl group which may be substituted by one or more substituents;

[7] The compound according to any one of the above [1]-[6] wherein at least one of $R^2$ and $R^3$ are an aryl group, a tert-alkyl group or a sec-alkyl group which may be substituted by one or more substituents;

[8] The compound according to any one of the above [1]-[4] or [6]-[7] wherein
 $R^1$ is a perfluoroalkyl group, or an alkyl group substituted by one or more perfluoroalkyl groups; and
 $R^2$ and $R^3$ are a phenyl group which may be substituted by one or more substituents;

[9] The compound according to any one of the above [1]-[4] or [6]-[7] wherein
 $R^1$ is an n-butyl group, a sec-butyl group, a tert-butyl group or a phenyl group which may have one or more substituents, and
 at least one of $R^2$ and $R^3$ are a perfluoroalkyl group or an alkyl group which is substituted by one or more perfluoroalkyl groups;

[10] The compound according to the above [3], [4], [8] or [9] wherein the perfluoroalkyl group is —$C_mF_{2m+1}$ wherein m represents an integer of 1-16;

[11] A process for preparing the compound of the formula (I) described in the above [1] comprising the following steps:
(i) reacting a compound of the formula (II):

$$\underset{R^2}{\overset{NO_2}{\diagup}}\diagdown_{R^3}$$

wherein: $R^2$ and $R^3$ are as defined in the above [1] with a compound of the formula (III):

$$R^1L \qquad\qquad (III)$$

wherein:
 $R^1$ is as defined in the above [1];
 L represents $MX_t$;
 M represents Li, Zn, Na, K, Al, Cu, B, Si, Ti, Cr, Fe, Ni, Pd, Pt, Rh, Ru, Ir, Mg or Sm;
 X represents a halogen atom or an alkoxy group; and
 t represents an integer of 0-6; and then,
(ii) dehydrating;

[12] A composition applied to a material containing a group reactive with a nitrileoxide group which comprises one or more compounds according to any one of the above [1]-[10];

[13] The composition according to the above [12] which is a surface treatment agent;

[14] The composition according to the above [12] which is a modifying agent;

[15] An article comprising a base material and a layer which is formed from the surface treatment agent according to the above [13] on the surface of the base material; and

[16] A modified polymer material treated with the modifying agent according to the above [14].

Effect of the Invention

The nitrileoxide compound of the present invention can have an arbitrary substituent and exhibit superior stability, in particular thermal stability. Additionally, the compound of the present invention can be used as a surface treatment agent, a modifying agent, a filler modifier, a reactive compatibilizing agent and a fiber treatment agent, and provide superior effects. In particular, a nitrileoxide compound having a perfluoroalkyl group can be used for surface treatment of various base materials (glass, general purpose rubber, polymer, and the like), and provide excellent water-repellency, oil-repellency.

EMBODIMENTS TO CARRY OUT THE INVENTION

In the present specification, unless otherwise specified, "a hydrocarbon group" means a group containing a carbon atom and a hydrogen atom (provided that, a part of or all of hydrogen atoms may be replaced with the following substituents). Examples of the hydrocarbon group include, but are not particularly limited to, for example, an aliphatic hydrocarbon group, an aromatic hydrocarbon group, and the like, which may be substituted by one or more substituents, a hydrocarbon group having 1-20 carbon atoms. It is noted that the hydrocarbon group may have one or more N, O, S, or the like at its end or in its molecular chain.

In the present specification, unless otherwise specified, the "aliphatic hydrocarbon group" may be straight, branched or cyclic and saturated or unsaturated, and may contain one or more rings. Examples of the "aliphatic hydrocarbon group" include, but are not particularly limited to, an alkyl group, an alkenyl group, an alkynyl group, a cycloalkyl group, a cycloalkenyl group. The "aliphatic hydrocarbon group" may be substituted by one or more substituents.

In the present specification, unless otherwise specified, the "alkyl group" may be straight or branched, and is for example an alkyl group having 1-20, preferably 1-12, more preferably 1-6 carbon atoms. Examples of the "alkyl group" include, but are not particularly limited to, a methyl group, an ethyl group, a propyl group, an isopropyl group, an n-butyl group, an isobutyl group, a sec-butyl group, a tert-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, an n-hexyl group, a 1-methylpentyl group, a 2-methylpentyl group, a 3-methylpentyl group, a 4-methylpentyl group, an n-hexyl group, a 2-methylpentyl group, a 3-methylpentyl group, a 4-methylpentyl group, a 1-ethylbutyl group, a 2-ethylbutyl group, a 1,1-dimethylbutyl group, a 1,2-dimethylbutyl group, a 1,3-dimethylbutyl group, a 2,2-dimethylbutyl group, a 2,3- dimethylbutyl group, a 3,3-dimethylbutyl group, a 1,1,2-trimethylpropyl group, a 1,2,2-trimethylpropyl group, a 1-ethyl-1-methylpropyl group, a 1-ethyl-2-methylpropyl group, and the like. The "alkyl group" may be substituted by one or more substituents.

In the present specification, unless otherwise specified, the "alkenyl group" may be straight or branched, and is for example an alkenyl group having 2-20, preferably 2-12, more preferably 2-6 carbon atoms. Examples of the "alkenyl group" include, but are not particularly limited to, for example, a group which at least one carbon-carbon single bond in the above alkyl group is replaced with a carbon-carbon double bond, specifically, a vinyl group, an allyl group, a 1-propenyl group, an isopropenyl group, a 2-methyl-1-propenyl group, a 2-methyl-2-propenyl group, a 1-butenyl group, a 2-butenyl group, a 3-butenyl group, a 1-pentenyl group, a 1-hexenyl group, a 1,3-hexadienyl group, a 1,5-hexadienyl group, and the like. The "alkenyl group" may be substituted by one or more substituents.

In the present specification, unless otherwise specified, the "alkynyl group" may be straight or branched, and is for example an alkynyl group having 2-20, preferably 2-12, more preferably 2-6 carbon atoms. Examples of the "alkynyl group" include, but are not particularly limited to, for example, a group which at least one carbon-carbon single bond in the above alkyl group is replaced with a carbon-carbon triple bond, specifically, an ethynyl group, a 1-propynyl group, a 2-propynyl group, a 1-butynyl group, a 2-butynyl group, a 3-butynyl group, a 1-methyl-2-propynyl group, a 1-pentynyl group, a 1-ethyl-2-propynyl group, a 1-hexynyl group, a 2-hexynyl group, and the like. The "alkynyl group" may be substituted by one or more substituents.

In the present specification, unless otherwise specified, the "cycloalkyl group" is a cyclic alkyl group having 3-20, preferably 5-12 carbon atoms. Examples of the "cycloalkyl group" include, but are not particularly limited to, for example, a cyclopropyl group, a cyclobutyl group, a cyclopentyl group, a cyclohexyl group, a cycloheptyl group, a cyclooctyl group, and the like. The "cycloalkyl group" may be substituted by one or more substituents.

In the present specification, unless otherwise specified, the "cycloalkenyl group" is a cyclic alkenyl group having 3-20, preferably 5-12 carbon atoms. Examples of the "cycloalkenyl group" include, but are not particularly limited to, for example, a cyclopropenyl group, a cyclobutenyl group, a cyclopentenyl group, a cyclohexenyl group, a cycloheptenyl group, a cyclooctenyl group, and the like. The "cycloalkenyl group" may be substituted by one or more substituents.

In the present specification, unless otherwise specified, the "aromatic hydrocarbon group (hereinafter, referred to as an aryl group)" may be monocyclic or polycyclic, for example bicyclic or tricyclic, or may be an aromatic heterocyclic group (hereinafter, referred to as a heteroaryl group). Examples of the "aromatic hydrocarbon group" include, but are not particularly limited to, an aryl group having 3-20 carbon atoms such as a phenyl group, a naphthyl group, and a heteroaryl group having 3-20 carbon atoms such as a furyl group, a thienyl group, a pyridyl group, an indolyl group, a quinolyl group, an isoquinolyl group, or an imidazolyl group. The "aromatic hydrocarbon group" may be substituted by one or more substituents.

In the present specification, unless otherwise specified, examples of the substituents for the hydrocarbon group, the alkyl group, the alkenyl group, the alkynyl group, the cycloalkyl group, the cycloalkenyl group and the aromatic hydrocarbon group include, but are not particularly limited to, for example, an oxygen atom; a halogen atom; a hydroxyl group; an unsubstituted, mono-substituted or di-substituted amino group; a nitro group; an azide group; a $C_{1-16}$ alkyl group, a $C_{2-16}$ alkenyl group, a $C_{2-16}$ alkynyl group, a $C_{3-16}$ cycloalkyl group, a $C_{3-16}$ cycloalkenyl group, a $C_{6-16}$ heterocycloalkyl group, a $C_{6-16}$ heterocycloalkenyl group, a $C_{6-16}$ aryl group, a $C_{6-16}$ heteroaryl group, a $C_{1-16}$ alkoxy group, a $C_{6-16}$ aryloxy, a $C_{1-16}$ alkylthio or a $C_{1-20}$ (poly) alkyl ether group which may be substituted by one or more halogen atoms; —O—C(O)—OR$^a$, —O—C(O)—NR$^a{}_2$, —C(O)—R$^a$, —C(O)—OR$^a$, —NR$^a$—C(O)—R$^a$, —NR$^a$—C(NR$^a$)—R$^a$, —C(NR$^a$)—R$^a$ or —C(NR$^a$)—NR$^a$2 (wherein R$^a$ represents each independently a hydrogen atom, a $C_{1-16}$ alkyl group, a $C_{2-16}$ alkenyl group, a $C_{2-16}$ alkynyl group, a $C_{3-16}$ cycloalkyl group, a $C_{3-16}$ cycloalkenyl group, a $C_{6-16}$ heterocycloalkyl group, a $C_{6-16}$ heterocycloalkenyl group, a $C_{6-16}$ aryl group or a $C_{6-16}$ heteroaryl group)

The "mono-substituted amino group" represents an amino group substituted by one substituent independently selected from the group consisting of a $C_{1-16}$ alkyl group, a $C_{2-16}$ alkenyl group, a $C_{2-16}$ alkynyl group, a $C_{3-16}$ cycloalkyl group, a $C_{3-16}$ a cycloalkenyl group, a $C_{6-16}$ heterocycloalkyl group, a $C_{6-16}$ heterocycloalkenyl group, a $C_{6-16}$ aryl group and a $C_{6-16}$ heteroaryl group, but is not particularly limited thereto. Examples of the "mono-substituted amino group" include, but are not particularly limited to, methylamino, ethylamino, phenylamino, and the like.

The "di-substituted amino group" represents an amino group substituted by two substituents independently selected from the group consisting of a $C_{1-16}$ alkyl group, a $C_{2-16}$ alkenyl group, a $C_{2-16}$ alkynyl group, a $C_{3-16}$ cycloalkyl group, a $C_{3-16}$ a cycloalkenyl group, a $C_{6-16}$ heterocycloalkyl group, a $C_{6-16}$ heterocycloalkenyl group, a $C_{6-16}$ aryl group and a $C_{6-16}$ heteroaryl group, but are not particularly limited thereto. Examples of the "di-substituted amino group" include, but are not particularly limited to, dimethylamino, diethylamino, diphenylamino, and the like.

Examples of the "$C_{1-16}$ alkoxy group" include, but are not particularly limited to, for example, a methoxy group, an ethoxy group, an n-propoxy group, an isopropoxy group, an n-butoxy group, an isobutoxy group, a sec-butoxy group, a tert-butoxy group, an n-pentyloxy group, an isopentyloxy group, a neopentyloxy group, a tert-pentyloxy group, a 1-ethylpropoxy group, an n-hexyloxy group, an isohexyloxy group, a neohexyloxy group, a 2-ethylbutoxy group, and the like.

Examples of the "$C_{6-16}$ aryloxy" include, but are not particularly limited to, for example, phenoxy, naphthyloxy, and the like.

Examples of the "$C_{1-16}$ alkylthio" include, but are not particularly limited to, for example, methylthio, ethylthio, propylthio, isopropylthio, butylthio, sec-butylthio, tert-butylthio, and the like.

In the present specification, unless otherwise specified, the "halogen (or halogen atom)" means a fluorine atom, a chlorine atom, a bromine atom, an iodine atom, and the like.

In the present specification, unless otherwise specified, the "perfluoroalkyl group" means a group which all hydrogen atoms in the above alkyl group are replaced with a fluorine atom, and is represented by —$C_mF_{2m+1}$ wherein m is an integer, specifically an integer of 1-16, for example an integer of 1-12 or 1-6. The "perfluoroalkyl group" may be straight or branched, preferably straight.

In the present specification, there is a case that a carbon atom to which a nitrileoxide group directly attached in the nitrileoxide compound is referred to as "$C^a$".

Hereinafter, the compound of the present invention will be described below.

The present invention provides a compound of the formula (I) (hereinafter, referred to as "compound (I) of the present invention"):

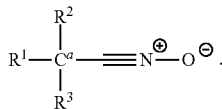

In the above formula (I), $R^1$ represents a hydrocarbon group. Examples of the hydrocarbon groups include, but are not particularly limited to, an alkyl group, an alkenyl group, an alkynyl group, a cycloalkyl group, a heterocycloalkyl group, an aryl group or a heteroaryl group, wherein these groups may have one or more substituents.

In one embodiment, $R^1$ is a fluoroalkyl group or a group (for example, an alkyl group) substituted by one or more fluoroalkyl groups. Preferably, the fluoroalkyl group is a fluoroalkyl group wherein a terminal carbon atom is $CF_2H$— and the other carbon atoms are fully substituted by a fluorine atom, or a perfluoroalkyl group, more preferably a perfluoroalkyl group.

Alternatively, $R^1$ may be a group of the formula (a):

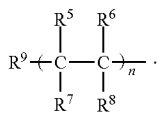

In the above formula (a), $R^5$, $R^6$, $R^7$ and $R^8$ represent each independently a hydrogen atom, a halogen atom, an alkyl group which may be substituted by a halogen atom, or —C(O)O$R^{10}$. Preferably, $R^5$, $R^6$, $R^7$ and $R^8$ may be each independently a hydrogen atom, a fluorine atom, a chlorine atom, an alkyl group which may be substituted by a fluorine atom or C(O)O$R^{10}$. The alkyl group which may be substituted by a fluorine atom is preferably a perfluoroalkyl group, more preferably trifluoromethyl group ($CF_3$).

$R^{10}$ represents a hydrogen atom or an alkyl group which may have one or more substituents. Preferably, $R^{10}$ is a fluoroalkyl group, more preferably a fluoroalkyl group wherein a terminal carbon atom is $CF_2H$— and the other carbon atoms are fully substituted by a fluorine atom, further preferably a perfluoroalkyl group.

In the above formula (a), $R^9$ represents a hydrogen atom, or an alkyl group which may have one or more substituents. Preferably, $R^9$ represents a hydrogen atom or an alkyl group optionally having a substituent, for example, $R^b$—C(O)-alkyl group, specifically, $R^b$—C(O)—C($R^{b'}$)($R^{b''}$)— (wherein $R^b$ represents an alkyl group or an aryl group, preferably an alkyl group, more preferably a methyl group; $R^{b'}$ represents an alkyl group, preferably a methyl group; $R^{b''}$ represents an alkyl group, preferably a methyl group).

In the above formula (a), n represents an integer of 1-10,000, preferably 1-1,000, more preferably 1-100.

In one embodiment, $R^1$ is $R^9$—$(CF_2CF_2)_n$—, $R^9$—$(CF_2CFCl)_n$—, $R^9$—$(CF_2CHF)_n$—, $R^9$—$(CF_2CH_2)_n$—, $R^9$—$(CFHCH_2)_n$—, R—$(CFClCH_2)_n$— or $R^9$—$(CF(CF_3)CH_2)_n$—.

In other embodiment, $R^1$ is a group of the formula (a'):

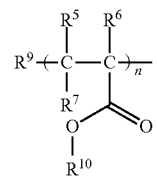

wherein $R^5$, $R^6$, $R^7$, $R^9$, $R^{10}$ and n are as defined above.

In the above formula (I), $R^2$ and $R^3$ represent each independently a hydrogen atom or hydrocarbon group. Examples of the hydrocarbon groups include, but are not particularly limited to, an alkyl group, a cycloalkyl group, a heterocycloalkyl group or an aryl group wherein the groups may have one or more substituents.

In one embodiment, one or both of $R^2$ and $R^3$ are each independently a fluoroalkyl group or a group (for example, an alkyl group, an aryl group) substituted by one or more fluoroalkyl groups. Preferably, the group substituted by one or more fluoroalkyl groups is a sec-alkyl group, a tert-alkyl group or a phenyl group substituted by one or more fluoroalkyl groups. Further preferably, the fluoroalkyl group is a fluoroalkyl group wherein a terminal carbon atom is $CF_2H$— and the other carbon atoms are fully substituted by a fluorine atom, more preferably a perfluoroalkyl group.

In the above formula (I), in at least one of $R^1$, $R^2$ and $R^3$, at least one hydrogen atoms are substituted by a fluorine atom, and $R^1$, $R^2$ and $R^3$ are respectively attached via its carbon atom to a carbon atom ($C^a$) to which a nitrileoxide group is attached.

In one embodiment, in the above formula (I), at least one of $R^1$, $R^2$ and $R^3$, for example, only $R^1$, $R^1$ and $R^2$, $R^2$ and $R^3$, or all of $R^1$, $R^2$ and $R^3$ are each independently a fluoroalkyl group, or a group substituted by one or more fluoroalkyl groups. Further preferably, the fluoroalkyl group is a fluoroalkyl group wherein a terminal carbon atom is $CF_2H$— and the other carbon atoms are fully substituted by a fluorine atom, more preferably a perfluoroalkyl group.

In a preferable embodiment, at least one, preferably at least two of $R^1$, $R^2$ and $R^3$ are a bulky group. The Examples of the "bulky group" included, but are not particularly limited to, the following groups:

(i) with respect to $R^1$:
a tert-alkyl group, a sec-alkyl group, a cycloalkyl group, a heterocycloalkyl group, an aryl group or a heteroaryl group which may be substituted by one or more substituents, or a group of the formula (a):

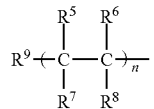

wherein $R^5$, $R^6$, $R^7$, $R^8$, $R^9$ and n are as defined above, (ii) with respect to $R^2$ and $R^3$:
an aryl group, a tert-alkyl group or a sec-alkyl group which may be substituted by one or more substituents.

In this embodiment, preferably one or both of $R^2$ and $R^3$ are an aryl group, a tert-alkyl group or a sec-alkyl group which may be substituted by one or more substituents.

In further preferable embodiment, $R^1$ is a perfluoroalkyl group or an alkyl group substituted by one or more perfluoroalkyl groups, and $R^2$ and $R^3$ are a phenyl group substituted by one or more substituents.

In other preferable embodiment, $R^1$ is an n-butyl group, a sec-butyl group, a tert-butyl group or a phenyl group which may have one or more substituents, and at least one of $R^2$ and $R^3$ are a perfluoroalkyl group or an alkyl group substituted by one or more perfluoroalkyl groups.

The compound of the present invention has superior stability, in particular thermal stability to a conventional aromatic nitrileoxide, and can be suitably used in various applications. Additionally, since an arbitrary substituent can be introduced by the process for producing, the compound of the present invention can be designed such that the compound has superior stability and reactivity within the desired temperature range.

Next, the process for producing the compound of the present invention will be described.

The compound of the formula (I) of the present invention can be produced by a process for preparing the compound of the formula (I) described in claim 1 comprising the following steps:

(i) reacting a compound of the formula (II):

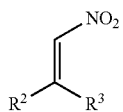

wherein: $R^2$ and $R^3$ are as defined above with a compound of the formula (III):

$$R^1L \quad \quad (III)$$

wherein:

$R^1$ is as defined above;

L represents $MX_t$;

M represents Li, Zn, Na, K, Al, Cu, B, Si, Ti, Cr, Fe, Ni, Pd, Pt, Rh, Ru, Ir, Mg or Sm;

X represents a halogen atom or an alkoxy group; and t represents an integer of 0-6; and then, (ii) dehydrating.

Firstly, Step (i) will be described.

The compound of the formula (II) is commercially available or can be produced by a known method.

For example, the compound of the formula (II) can be produced by reacting a ketone derivative ($R^1R^2C=O$) with nitromethane in a solvent, for example, THF in the presence of a strong base (for example, lithium bis(trimethylsilyl)amido, and the like) as shown in the following scheme. This reaction is generally known as a nitroaldol reaction, and can easily performed by those skilled in the art.

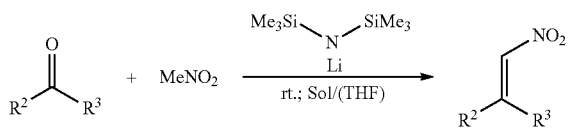

Alternatively, the compound of the formula (II) can be produced by reacting an imine derivative ($R^1R^2C=NH$) with nitromethane as shown in the following scheme.

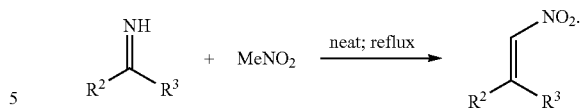

In the formula (III), L represents $MX_t$. M represents Li, Zn, Na, K, Al, Cu, B, Si, Ti, Cr, Fe, Ni, Pd, Pt, Rh, Ru, Ir, Mg or Sm, preferably Li, Zn, Na, Cu, B or Si, particularly preferably, Li or Mg (i.e. an organolithium reagent or Grignard reagent). X represents a halogen atom or an alkoxy group. t represents an integer of 0-6. The compound of the formula (III) is an agent having strong nucleophilicity, preferably Grignard reagent or alkyllitium. The compound can be produced by a known method from commercially available compound.

A molar ratio of the compound of the formula (II) to the compound of the formula (III) is, usually 1:1 to 1:5, preferably 1:1 to 1:2.

The reaction is performed usually in a solvent. The solvent is not limited as long as the nucleophile of the formula (III) is not quenched, and include, for example, THF, dichloromethane, 1,2-dichloroethane, HMPA (hexamethylphosphamide), DMPU (dimethylpropylene), TMEDA (tetramethylethylenediamine), or the mixture thereof.

A reaction temperature is appropriately selected depending on the nucleophile of the formula (III) used, for example, is a temperature at which the nucleophile d is not quenched. Those skilled in the art can determine such temperature.

A reaction time is usually 10 minutes to 24 hours, for example 1 to 3 hours.

The reaction may be performed in the presence of a catalyst. Examples of the catalyst include, but are not particularly limited to, HMPA (hexamethylphosphoric triamide), DMPU (N,N'-dimethylpropyleneurea), TMEDA (tetramethylethylenediamine), a crown ether, and the like.

Next, Step (ii) will be described.

The dehydration treatment can be performed by using concentrated sulfuric acid, trifluoromethanesulfonic acid, trifluoromethanesulfonimide or phenylisocyanate, or other strong acid having pair anion having no nucleophilicity, but are not particularly limited thereto.

A treatment temperature is usually 0° C. to a room temperature.

A treatment time is usually 1 minute to 60 minutes, for example 10 minutes to 30 minutes.

According to the process of the present invention, a nitrileoxyde compound of the formula (I) having an arbitrary substituent can be easily synthesized in one-pot.

Next, the composition of the present invention will be described.

The present invention provides a composition comprising one or more present compounds (I) described above and used for being applied to a material containing a group reactive with a nitrileoxide group (hereinafter, referred to as a "composition of the present invention"). The composition may be a liquid or a solid. In addition, the composition may consist of the above-mentioned compound (I) of the present invention.

Examples of the "group reactive with a nitrileoxide group" include a group having a double bond (C=C, C=N, N=N, C=S, P(V)=C, C=P(III), C=As, C=Se, B=N, P(V)=N, C=O), or a group having a triple bond (C=C, C=N, C=P), specifically an alkenyl group, an alkynyl group, and a nitrile group.

Examples of the "material" in the material containing a group reactive with a nitrileoxide group include, but are not particularly limited to, for example, a base material applied with the following surface treatment agent (e.g. a glass, a resin, etc.), a compound applied with a modifying agent, a compatibilizing agent, a cross-linking agent or a modifier of a liquid rubber or a rubber having a low-temperature properties, in particular a polymer compound (e.g. a natural rubber, a synthetic rubber) and a filler applied with a filler modifier.

In one embodiment, the composition of the present invention is a surface treatment agent.

The surface treatment agent of the present invention comprises at least one compound (I) of the present invention as a main ingredient or an active ingredient, and can form surface-treating layer having water-repellency, oil-repellency, antifouling property, friction durability, surface slip property, or the like, thus is used as an antifouling coating agent. The "main ingredient" means an ingredient whose contents is more than 50% in the surface treatment agent, and the "active ingredient" means an ingredient which remains on a material to be surface-treated to form a surface-treating layer, thereby exhibiting some function (water-repellency, oil-repellency, antifouling property, surface slip property, friction durability, etc.).

The surface treatment agent of the present invention has an advantageous than a surface treatment agent containing a fluorine-containing silane compound which is suitably applied mainly to a glass material, and a surface treatment agent containing a compound having a curable moiety (for example, double bond) which is suitably applied mainly to a resin material in point that it can be suitably applied to any base material as long as it is reactive with a nitrileoxide group.

The composition of the surface treatment agent of the present invention may be selected depending on a function which is desired in the surface-treating layer.

For example, the surface treatment agent may comprise a fluoropolyether compound which may be also understood as a fluorine-containing oil, preferably a perfluoro(poly)ether compound (hereinafter, referred to as a "fluorine-containing oil") in addition to compound (I) of the present invention. The fluorine-containing oil contributes to increasing of surface slip property of the surface-treating layer.

The fluorine-containing oil may be contained in the surface-treating agent of the present invention, for example, at 0-300 parts by mass, preferably 50-200 parts by mass with respect to 100 parts by mass of compound (I) of the present invention (as the total mass when two or more compounds are used; hereinafter the same shall apply).

Examples of the above-mentioned fluorine-containing oil include, but are not particularly limited to, for example, a compound (a perfluoropolyether compound) of the following general formula (A).

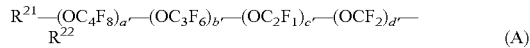
(A)

In the formula, $R^{21}$ represents an alkyl group having 1-16 carbon atoms which may be substituted by one or more fluorine atoms, preferably an alkyl group having 1-3 carbon atoms which may be substituted by one or more fluorine atoms. Preferably, the alkyl which may be substituted by one or more fluorine atoms is a fluoroalkyl group in which a terminal carbon atom is $CF_2H$— and the other carbon atoms are fully substituted by a fluorine atom, or a perfluoroalkyl group, more preferably a perfluoroalkyl group.

$R^{22}$ represents a hydrogen atom, a fluorine atom, or an alkyl group having 1-16 carbon atoms which may be substituted by one or more fluorine atoms, preferably an alkyl group having 1-3 carbon atoms which may be substituted by one or more fluorine atoms. Preferably, the alkyl which may be substituted by one or more fluorine atoms is a fluoroalkyl group in which a terminal carbon atom is $CF_2H$— and the other carbon atoms are fully substituted by a fluorine atom, or a perfluoroalkyl group, more preferably a perfluoroalkyl group.

Subscripts a', b', c' and d' represent the repeating number of each of three repeating units of perfluoropolyether which constitute a main backbone of the polymer, and are each independently an integer of 0 or more and 300 or less, and the sum of a', b', c' and d' is at least 1, preferably 1-100. The occurrence order of the respective repeating units in parentheses with the subscript a', b', c' or d' is not limited in the formula. Among these repeating units, the —$(OC_4F_8)$— group may be any of —$(OCF_2CF_2CF_2CF_2)$—, —$(OCF(CF_3)CF_2CF_2)$—, —$(OCF_2CF(CF_3)CF_2)$—, —$(OCF_2CF_2CF(CF_3))$—, —$(OC(CF_3)_2CF_2)$—, —$(OCF_2C(CF_3)_2)$—, —$(OCF(CF_3)CF(CF_3))$—, —$(OCF(C_2F_5)CF_2)$— and —$(OCF_2CF(C_2F_5))$—, preferably —$(OCF_2CF_2CF_2CF_2)$. The —$(OC_3F_6)$— group may be any of —$(OCF_2CF_2CF_2)$—, —$(OCF(CF_3)CF_2)$— and —$(OCF_2CF(CF_3))$—, preferably —$(OCF_2CF_2CF_2)$—. The —$(OC_2F_4)$— group may be any of —$(OCF_2CF_2)$— and —$(OCF(CF_3))$—, preferably —$(OCF_2CF_2)$—.

Examples of the perfluoropolyether compound of the above general formula (A) include a compound of any of the following general formulae (A1) and (A2) (may be one compound or a mixture of two or more compounds).

(A1)

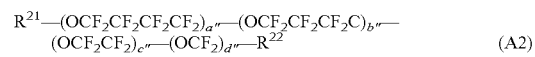
(A2)

In these formulae:

$R^{21}$ and $R^{22}$ are as defined above; in the formula (A1), b" is an integer of 1 or more and 100 or less; and in the formula (A2), a" and b" are each independently an integer of 1 or more and 30 or less, and c" and d" are each independently an integer of 1 or more and 300 or less. The occurrence order of the respective repeating units in parentheses with the subscript a", b", c" or d" is not limited in the formulae.

The compound of the general formula (A1) and the compound of the general formula (A2) may be used alone or in combination.

When compound (I) of the present invention contains a perfluoroalkyl group, the fluorine-containing oil may be a compound of the general formula $Rf^1$—F wherein $Rf^1$ is a perfluoroalkyl group contained in compound (I) of the present invention. In this case, the compound of $Rf^1$—F is preferable because the compound has high affinity for compound (I) of the present invention.

The surface treatment agent may comprise a silicone compound which may be also understood as a silicone oil (hereinafter referred to as a "silicone oil") in addition to compound (I) of the present invention. The silicone oil contributes to increasing of surface slip property of the surface-treating layer.

The silicone oil may be contained in the surface treatment agent, for example, at 0-300 parts by mass, preferably 50-200 parts by mass with respect to 100 parts by mass of compound (I) of the present invention.

Examples of the above-mentioned silicone oil include, for example, a liner or cyclic silicone oil having 2,000 or less siloxane bonds. The liner silicone oil may be so-called a straight silicone oil and a modified silicon oil. Examples of the straight silicone oil include dimethylsilicone oil, methylphenylsilicone oil, and methylhydrogensilicone cil. Examples of the modified silicone oil include that which is obtained by modifying a straight silicone oil with alkyl, aralkyl, polyether, higher fatty acid ester, fluoroalkyl, amino, epoxy, carboxyl, alcohol, or the like. Examples of the cyclic silicone oil include, for example, cyclic dimethylsiloxane oil.

The present invention also provides an article comprising a base material and a layer (a surface-treating layer) which is formed from the above-mentioned compound (I) of the present invention or the surface treatment agent (hereinafter, representatively referred to as a "surface-treating composition") on the surface of the base material. This article can be produced, for example, as follows.

Firstly, the base material is provided. As mentioned above, the surface treatment agent of the present invention can be suitably applied to any base material as long as it has reactivity with a nitrileoxide group. The base material usable in the present invention may be composed of any suitable material such as a glass, a resin (may be a natural or synthetic resin such as a common plastic material, and may be in form of a plate, a film, or others), a metal (may be a simple substance of a metal such as aluminum, copper, or iron, or a complex such as alloy or the like), a ceramic, a semiconductor (silicon, germanium, or the like), a fiber (a fabric, a non-woven fabric, or the like), a fur, a leather, a wood, a pottery, a stone, or the like.

For example, when an article to be produced is an optical member, a material constituting the surface of the base material may be a material for an optical member, for example, a glass or a transparent plastic. For example, when an article to be produced is an optical member, any layer (or film) such as a hard coating layer or an antireflection layer may be formed on the surface (outermost layer) of the base material. As the antireflection layer, either a single antireflection layer or a multi antireflection layer may be used. Examples of an inorganic material usable in the antireflection layer include $SiO_2$, $SiO$, $ZrO_2$, $TiO_2$, $TiO$, $Ti_2O_3$, $Ti_2O_5$, $Al_2O_3$, $Ta_2O_5$, $CeO_2$, $MgO$, $Y_2O_3$, $SnO_2$, $MgF_2$, $WO_3$, and the like. These inorganic materials may be used alone or in combination with two or more (for example, as a mixture). Furthermore, the base material may have an insulating layer, an adhesive layer, a protecting layer, a decorated frame layer (I-CON), an atomizing layer, a hard coating layer, a polarizing film, a phase difference film, a liquid crystal display module, and the like, depending on its specific specification.

The shape of the base material is not particularly limited. The region of the surface of the base material on which the surface-treating layer should be formed may be at least a part of the surface of the base material, and may be appropriately determined depending on use, the specific specification, and the like of the article to be produced.

The base material may be that of which at least the surface consists of a material originally having a group reactive with a nitrileoxide group. On the other hand, by pre-treating the base material, the group reactive with a nitrileoxide group may be introduced to the base material. For example, when the base material is a glass, the group reactive with a nitrileoxide group can be introduced to the base material by treating the base material with a piranha solution to express a hydroxyl group, and reacting this hydroxyl group for example with allyltrichlorosilane.

Next, the film of the above surface-treating agent of the present invention is formed on the surface of the base material, and the film is post-treated, as necessary, and thereby the surface-treating layer is formed from the surface-treating agent.

The formation of the film of the surface-treating agent of the present invention can be performed by applying the above surface-treating agent on the surface of the base material such that the surface-treating agent coats the surface. The method of coating is not particularly limited. For example, a wet coating method or a dry coating method can be used.

Examples of the wet coating method include dip coating, spin coating, flow coating, spray coating, roll coating, gravure coating, micro-gravure coating, bar coating, die coating, and a similar method.

Examples of the dry coating method include vacuum deposition, sputtering, CVD and a similar method. The specific examples of the vacuum deposition include resistance heating, electron beam, high-frequency heating, ion beam, and a similar method. The specific examples of the CVD method include plasma-CVD, optical CVD, thermal CVD and a similar method.

Additionally, coating can be performed by an atmospheric pressure plasma method.

When the wet coating method is used, the surface-treating agent of the present invention is diluted with a solvent, and then it is applied to the surface of the base material. In view of stability of the fluorine-containing compound or the composition and volatile property of the solvent, the following solvents are preferably used: an aliphatic perfluorohydrocarbon having 5-12 carbon atoms (for example, perfluorohexane, perfluoromethylcyclohexane and perfluoro-1,3-dimethylcyclohexane); an aromatic polyfluorohydrocarbon (for example, bis(trifluoromethyl) benzene); an aliphatic polyfluorohydrocarbon; a hydrofluoroether (HFE) (for example, an alkyl perfluoroalkyl ether such as perfluoropropyl methyl ether ($C_3F_7OCH_3$), perfluorobutyl methyl ether ($C_4F_9OCH_3$), perfluorobutyl ethyl ether ($C_4F_9OC_2H_5$), and perfluorohexyl methyl ether ($C_2F_5CF$ ($CCH_3$) $C_3F_7$) (the perfluoroalkyl group and the alkyl group may be liner or branched)), and the like. These solvents may be used alone or as a mixture of 2 or more compound. Among them, the hydrofluoroether is preferable, perfluorobutyl methyl ether ($C_4F_9OCH_3$) and/or perfluoroburyl ethyl ether ($C_4F_9OC_2H_5$) are particularly preferable.

After forming the film of the surface treatment agent by using the above method, if necessary, post-treatment may be performed. Examples of the post-treatment include, but are not particularly limited to, for example heating to 40-150° C., for example 60-100° C.

As described above, the surface-treating layer derived from the film of the surface-treating agent of the present invention is formed on the surface of the base material to produce the article of the present invention.

Therefore, the surface treatment agent can be suitably used to form the surface-treating layer on an outermost layer of an optical material. Examples of the optical material include preferably a variety of optical materials: for example, displays such as a cathode ray tube (CRT; for example, TV, personal computer monitor), a liquid crystal display, a plasma display, an organic EL display, an inorganic thin-film EL dot matrix display, a rear projection display, a vacuum fluorescent display (VFD), a field emission display (FED; Field Emission Display), or a protective plate of such displays, or that in which these displays and protective plates have been subjected to antireflection treatment on their surface.

The article having the surface-treating layer obtained according to the present invention is not specifically limited to, but may be an optical member. Examples of the optical member include the followings: lens of glasses, or the like; a front surface protective plate, an antireflection plate, a polarizing plate, or an anti-glare plate on a display such as PDP and LCD; a touch panel sheet of an instrument such as a mobile phone or a personal digital assistance; a disk surface of an optical disk such as a Blu-ray disk, a DVD disk, a CD-R or MO; an optical fiber, and the like.

The thickness of the surface-treating layer is not specifically limited. For the optical member, the thickness of the surface-treating layer is within the range of 0.1-30 µm, preferably 0.5-20 µm, in view of optical performance, friction durability and antifouling property.

The surface-treating layer formed from the surface treatment agent of the present invention may have water-repellency, oil-repellency, antifouling property, surface slip property and/or high friction durability, thus may be suitably used as a functional thin film.

In one embodiment, the composition of the present invention is a modifying agent.

The modifying agent of the present invention comprises at least one compound (I) of the present invention described above and can modify solubility in an organic solvent of a base material, for example, a polymer material.

Thought, the modifying agent of the present invention can exhibit a function even when it contains only compound (I) of the present invention, the modifying agent may further contain a solvent.

Examples of the solvents described above are not particularly limited as long as it can dissolve compound (I) of the present invention or can be compatible with compound (I) of the present invention, and include, for example, a fluorine-containing aliphatic or aromatic hydrocarbons, and the like, in particular, perfluorohexane, bis(trifluoromethyl) benzene, and the like.

The modifying agent of the present invention can be suitably applied to any base material (for example, polymer material) as long as it has reactivity with a nitrileoxide group.

Examples of the polymer materials include, but are not particularly limited to, PAN (polyacrylonitrile) having a nitrile group (C≡N) in the molecular, NR (natural rubber) having a carbon-carbon double bond (C═C) in the molecular, EPDM (ethylene-propylene-diene copolymer rubber), NBR (nitrile rubber) having a nitrile group and a carbon-carbon double bond in the molecular, and the like.

Modifying treatment using the modifying agent of the present invention can be carried out by contacting compound (I) of the present invention with a polymer material in an organic solvent or without a solvent, although the present invention is not particularly limited thereto.

The solvents described above are, but not particularly limited to, preferably a solvent in which both the polymer material and compound (I) of the present invention are easily dissolved. Specifically, it includes chloroform, DMF (N,N-dimethylformamide), and the like.

When the treatment is carried out in the absence of a solvent, the treatment may be carried out under air or an atmosphere where inert gas is filled.

Examples of the inert gases include, but are not particularly limited to, argon, nitrogen, and the like.

When the modifying treatment is carried out in the absence of a solvent, the modifying treatment is preferably carried out in a kneader.

Examples of the kneader include, but are not particularly limited to, kneaders such as a biaxial kneader, an internal mixer, and a Banbury mixer, or extruders such as a twin-screw extruder, a single screw extruder and a multi-screw extruder, and the like.

A temperature of the modifying treatment is not particularly limited as long as compound (I) of the present invention can be reacted with the polymer material at the temperature, is preferably 0-150° C. since the chemical reaction is facilitated at higher temperature, on the other hand, a management of the manufacturing process is easy if a temperature control such as heating is not performed. Furthermore, the temperature is more preferably 20-100° C. when the polymer material is a polymer which has at least carbon-carbon double bond as a multiple bond, for example, NBR, NR, EPDM, or the like, and the temperature is more preferably 60-150° C. when the polymer material is a polymer which has only carbon-carbon triple bond as a multiple bond, for example, PAN or the like.

Additionally, the present invention provides a modified material, for example a modified polymer material, treated with the modifying agent described above.

In the modified polymer material treated with the modifying agent of the present invention, its solubility in various organic solvent is varied, and its resistance to sunlight and ozone is improved, as a result of which its durability is improved.

In one embodiment, the composition of the present invention is a filler modifier.

The filler modifier of the present invention comprises at least one compound (I) of the present invention.

Examples of the filler to which the filler modifier of the present invention is applied include a filler having a group reactive with a nitrileoxide group on its surface, for example, but are not particularly limited to, silica particles, alumina, titanium oxide, barium oxide and calcium oxide in which a group having an unsaturated bond such as a vinyl group, an allyl group, and a nitrile group is introduced on its surface.

The method for introducing the group having an unsaturated bond such as a vinyl group, an allyl group, and a nitrile group to the surface of silica particles is well known by those skilled in the art. For example, introduction of a vinyl group to the surface of the silica particles can be carried out by treating the silica particles with a vinyl-based silane coupling agent (e.g. vinylethoxysilane, or the like).

The modification treatment using the filler modifier can be carried out simply by mixing the filler modifier with the filler. The modification treatment is carried out in a solvent.

Examples of the solvent are not particularly limited as long as it is inert to the compound of the present invention and the filler, and include, for example, water, an aliphatic perfluorohydrocarbon having 5-12 carbon atoms (for example, perfluorohexane, oerfluoromethylcyclohexane and perfluoro-1,3-dimethylcyclohexane); an aromatic polyfluorohydrocarbon (for example, bis(trifluoromethyl)benzene); an aliphatic polyfluorohydrocarbon; a hydrofluoroether (HFE) (for example, an alkyl perfluoroalkyl ether such as perfluoropropyl methyl ether ($C_3F_7OCH_3$), perfluorobutyl methyl ether ($C_4F_9OCH_3$), perfluorobutyl ethyl ether ($C_4F_9OCH_5$), and perfluorohexyl methyl ether ($C_2F_5CF(OCH_3)C_3F_7$) (the perfluoroalkyl group and the alkyl group may be liner or branched)), and the like.

The present invention also provides a filler which is treated with the filler modifier, for example silica particles.

The filler which is treated with the filler modifier has effects, for example when it is used as a filler for a fluorine rubber, a perfluoro rubber or a fluororesin, dispersibility is improved or a reaction of a reactive group on the surface of the filler (for example, $SiO_2$ in silica) with a fluorine-containing polymer can be suppressed in comparison with an untreated filler.

In one embodiment, the composition of the present invention is a reactive compatibilizing agent.

The reactive compatibilizing agent of the invention comprises at least one the above mentioned compound (I) of the present invention, and can improve compatibility between two or more materials (compounds), for example, between a general-purpose polymer reactive with a nitrileoxide group and a fluorine-containing polymer.

The reactive compatibilizing agent of the present invention can be applied to any combination of compounds as long as it is a combination of a compound reactive with a nitrileoxide group and a fluorine-containing compound. In addition, a combination of compounds to be compatibilized (be complexed) may be a combination of three or more compounds, for example, one compound reactive with a nitrileoxide group and two fluorine-containing compounds.

Examples of the compound reactive with a nitrileoxide group include, but are not particularly limited to, a general-purpose polymer having a moiety reactive with a nitrileoxide group (e.g. C=C, C≡N) in its molecular, for example, a natural rubber, NBR (nitrile rubber), EPDM (ethylene-propylene-diene copolymerized rubber), PAN (polyacrylonitrile) and $H_2C=C(R)-(CH_2-CHR)_n-CH_2-CR=CH_2$ (wherein R is each independently a hydrogen atom, a methyl group, an ethyl group or an isobutyl group, and n is an integer of 10-1000).

Examples of the fluorine-containing compound include, but are not particularly limited to, a fluororesin, a fluorine rubber, and the like.

Examples of the fluororesin include a non-melt processable fluororesin, for example, polytetrafluoroethylene (PTFE), and a melt processable fluororesin, and the like.

The PTFE may be a homopolymer of tetrafluoroethylene (TFE), or a modified polytetrafluoroethylene (modified PTFE). In the present specification, "modified PTFE" means a polymer obtained by co-polymerizing TFE with a co-monomer in such a small amount as not to provide melt processability to the resulting copolymer. Examples of the small amount of co-monomer include, but are not limited to, for example, hexafluoropropylene (HFP), chlorotrifluoroethylene (CTFE), trifluoroethylene (TrFE), a perfluoro(alkyl vinyl ether) (PAVE), a perfluoro(alkoxyalkyl vinyl ether), a (perfluoroalkyl)ethylene, and the like. The small amount of co-monomer can be used alone or two or more.

Examples of the PAVE include perfluoro(methylvinyl ether), perfluoro(ethylvinyl ether), perfluoro(propylvinyl ether), and the like.

A ratio of the small amount of co-monomer added to the modified PTFE is, when PAVE, a perfluoro(alkoxyalkyl vinyl ether), or the like is used, usually 0.001-1% by mass with respect to the total mass of TFE and the small amount of copolymer, but it is difficult depending on the type.

Examples of the melt processable fluororesin include a tetrafluoroethylene (TFE)/hexafluoropropylene (HFP) copolymer, a TFE/HFP/perfluoro(alkyl vinyl ether) (PAVE) copolymer, a TFE/PAVE copolymer (tetrafluoroethylene-perfluoroalkyl vinyl ether copolymer (PFA) and a tetrafluoroethylene-perfluoro methyl vinyl ether copolymer (MFA)), an ethylene (Et)/TFE copolymer, an Et/TFE/HFP copolymer, polychlorotrifluoroethylene (PCTFE), a chlorotrifluoroethylene (CTFE)/TFE copolymer, an Et/CTFE copolymer, a TFE/vinylidene fluoride (VDF) copolymer, a VDF/HFP/TFE copolymer, a VDF/HFP copolymer, and the like.

Examples of the fluororesin further include a hydroxyl group containing and fluorine containing copolymer containing a fluoroolefin unit and a hydroxyl group-containing radical polymerizable unsaturated monomer unit.

Examples of the fluoroolefin unit include one or more of a tetrafluoroethylene (TFE) unit, a chlorotrifluoroethylene (CTFE) unit, a vinyl fluoride (VF) unit, a vinylidene fluoride (VDF) unit, a hexafluoropropylene (HFP) unit, a trifluoroethylene (TrFE) unit, a perfluoro(alkyl vinyl ether) (PAVE) unit. Examples of the PAVE unit include a perfluoromethyl vinyl ether unit and a perfluoropropylvinyl ether unit.

Examples of the combination of two or more units comprising the TFE unit include a TFE/HFP unit, a TFE/PAVE unit, a TFE/ethylene unit, a TFE/vinyl ether unit, a TFE/vinyl ester unit, a TFE/vinyl ester/vinyl ether unit, a TFE/vinyl ether/allyl ether unit, and the like. Among them, in view of readily mixing with an ethylenically unsaturated group-containing monomer, the TFE/ethylene unit, the TFE/vinyl ether unit, the TFE/vinyl ester unit, the TFE/vinyl ester/vinyl ether unit, the TFE/vinyl ether/allyl ether unit, or the like is preferable.

Examples of the combination of two or more units comprising the CTFE unit include a CTFE/HFP unit, a CTFE/PAVE unit, a CTFE/ethylene unit, a CTFE/vinyl ether unit, a CTFE/vinyl ester unit, a CTFE/vinyl ester/vinyl ether unit, a CTFE/vinyl ether/allyl ether unit, and the like. Among them, in view of readily mixing with an ethylenically unsaturated group-containing monomer, the CTFE/ethylene unit, the CTFE/vinyl ether unit, the CTFE/vinyl ester unit, the CTFE/vinyl ester/vinyl ether unit, the CTFE/vinyl ether/allyl ether unit, or the like is preferable.

Examples of the combination of two or more units comprising the HFP unit include a CTFE/HFP unit, a TFE/HFP unit, a HFP/vinyl ether unit, a HFP/vinyl ester unit, a HFP/vinyl ester/vinyl ether unit, a HFP/vinyl ether/allyl ether unit, and the like. Among them, in view of readily mixing with an ethylenically unsaturated group-containing monomer, the HFP/vinyl ether unit, the HFP/vinyl ester unit, the HFP/vinyl ester/vinyl ether unit, the HFP/vinyl ether/allyl ether unit, or the like is preferable.

Examples of the combination of two or more units comprising the VDF unit include a VDF/TFE unit, a VDF/HFP unit, a VDF/TFE/HFP unit, a VDF/CTFE unit, a VDF/TFE/PAVE unit, a VDF/CTFE/TFE unit, a VDF/CTFE/HFP unit, and the like. Among them, in view of readily mixing with an ethylenically unsaturated group-containing monomer, it is preferable that the VDF unit is contained in the polymer at 50 mol % or more.

Specific examples of the hydroxyl group-containing radical polymerizable unsaturated monomer unit of the hydroxyl group containing and fluorine containing copolymer include, for example, a hydroxyalkyl vinyl ether or a hydroxyalkyl allyl ether of the formula:

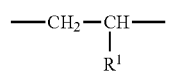

wherein $R^1$ is $-OR^2$ or $-CH_2OR^2$ (wherein $R^2$ is an alkyl group having a hydroxyl group). $R^2$ is, for example, a group which 1-3 hydroxyl groups, preferably one hydroxyl group is linked to a straight or branched alkyl group having 1-8 carbon atoms. Examples of them include, for example, a 2-hydroxyethylvinyl ether unit, a 3-hydroxypropylvinyl ether unit, a 2-hydroxypropylvinyl ether unit, a 2-hydroxy-2-methylpropylvinyl ether unit, a 4-hydroxybutylvinyl ether unit, a 4-hydroxy-2-methylbutylvinyl ether unit, a 5-hydroxypentylvinyl ether unit, 6-hydroxyhexylvinyl ether unit, a 2-hydroxyethylallyl ether unit, a 4-hydroxybutylallyl ether unit, an ethylene glycol monoallyl ether unit, a diethylene glycol monoallyl ether unit, a triethylene glycol monoallyl ether unit, a glycerin monoallyl ether unit, and the like. Among them, a hydroxyalkyl vinyl ether having 1-3 carbon atoms is particularly preferable, and a 4-hydroxybutylvinyl ether unit or a 2-hydroxyethylvinyl ether unit is more preferable in view of easy polymerization.

The hydroxyl group containing and fluorine containing copolymer may further comprise a hydroxyl-free and fluorine-free vinyl ether unit and/or a fluorine-free vinyl ester unit Specific examples of the hydroxyl group-free and fluorine-free vinyl ether unit and/or the fluorine-free vinyl ester unit in the hydroxyl group containing and fluorine containing copolymer include, for example, an alkyl vinyl ether or an alkyl allyl ether of the formula:

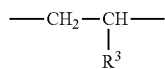

wherein $R^3$ is $-OR^4$, $-COOR^4$ or $-OCOR^4$ (wherein $R^4$ is an alkyl group). $R^4$ is, for example, a straight, branched or cyclic alkyl group having 1-8 carbon atoms. As examples of them, for example, a cyclohexylvinyl ether unit, a methylvinyl ether unit, an ethylvinyl ether unit, a propylvinyl ether unit, an n-butylvinyl ether unit, an isobutylvinyl ether unit, a vinyl acetate unit, a vinyl propionate unit, a vinyl butyrate unit, a vinyl isobutyrate unit, a vinyl pivalate unit, a vinyl caproate unit, a vinyl versatate unit, a vinyl laurate unit, a vinyl stearate unit or a vinyl cyclohexyl carboxylate unit is preferable.

Furthermore, in view of excellent weather resistance, solubility and low-cost, vinyl versatate, vinyl laurate, vinyl stearate, a vinyl cyclohexyl carboxylate, or vinyl acetate is preferable. Among them, in view of chemical resistance, a non-aromatic vinyl carboxylate ester, in particular a carboxylic acid vinyl ester having 6 or more carbon atoms in carboxylic acid is preferable, and a carboxylic acid vinyl ester having 9 or more carbon atoms in carboxylic acid is more preferable. The upper limit of carbon atoms of carboxylic acid in the carboxylic acid vinyl ester is preferably 20 or less, more preferably 15 or more. As a specific example, vinyl versatate is most preferably.

The hydroxyl group containing and fluorine containing copolymer may contain a carboxyl group-containing monomer unit.

The carboxyl group-containing monomer unit contains a carboxyl group and does not contain a hydroxyl group and an aromatic group, and in this point, it differs from the other units.

Examples of the carboxyl group-containing monomer unit include, for example, a carboxyl group-containing vinyl monomer of the formula:

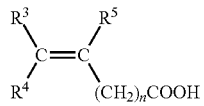

wherein $R^3$, $R^4$ and $R^5$ is same or different, and are a hydrogen atom, an alkyl group, a carboxyl group or an ester group, and n is 0 or 1 or the formula:

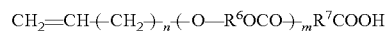

wherein $R^6$ and $R^7$ are same or different, and are a saturated or unsaturated straight or cyclic alkyl group, n is 0 or 1, and m is 0 or 1.

Specific examples of the carboxyl group-containing monomer unit include, for example, one or more selected from acrylic acid, methacrylic acid, vinyl acetate, crotonic acid, cinnamic acid, 3-allyloxy propionic acid, itaconic acid, itaconic acid monoester, maleic acid, maleic acid monoester, maleic anhydride, fumaric acid, fumaric acid monoester, vinyl phthalate and vinyl pyromellitate. Among them, crotonic acid, itaconic acid, maleic acid, maleic acid monoester, fumaric acid, fumaric acid monoester, and 3-allyloxy propionic acid which have low homopolymerizality are preferable.

The lower limit of the ratio of carboxyl group-containing monomer unit is 0.1 mol %, preferably 0.4 mol %, and the upper limit is 2.0 mol %, preferably 1.5 mol %.

Specific examples of the hydroxyl group containing and fluorine containing copolymer include, for example, following compounds:

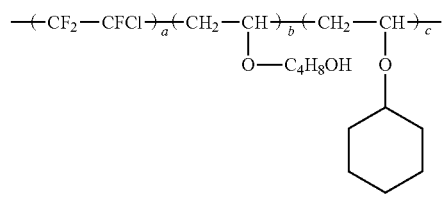

(wherein the formula, the ratio by mole of a, b, and c is a:b:c=40 to 60:3 to 15:5 to 45);

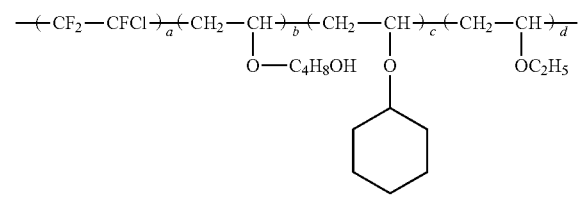

(wherein the formula, the ratio by mole of a, b, and c is a:b:c=40 to 60:3 to 15:5 to 45:5 to 45);

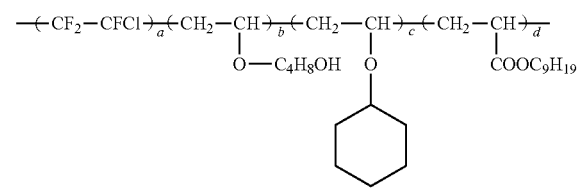

(wherein the formula, the ratio by mole of a, b, c and d is a:b:c:d=40 to 60:3 to 15:5 to 45:5 to 45);

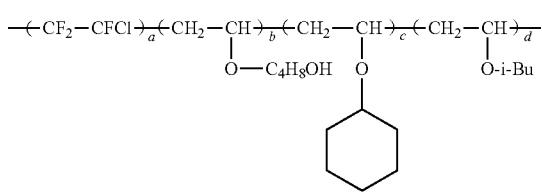

(wherein the formula, the ratio by mole of a, b, c and d is a:b:c:d=40 to 60:3 to 15:5 to 45:5 to 45, and i-Bu represents an isobutyl group); tetrafluoroethylene/vinyl versatate/hydroxybutyl vinyl ether; tetrafluoroethylene/vinyl versatate/hydroxyethyl vinyl ether/tert-butyl vinyl benzoate; tetrafluoroethylene/vinyl versatate/hydroxybutyl vinyl ether/crotonic acid; and tetrafluoroethylene/vinyl versatate/hydroxyethyl vinyl ether/vinyl benzoate/crotonic acid.

Examples of the fluorine rubber include a non-perfluoro fluorine rubber and a perfluoro fluorine rubber.

Examples of the non-perfluoro fluorine rubber include a vinylidene fluoride (VDF) fluorine rubber, tetrafluoroethylene (TFE)/propylene (Pr) fluorine rubber, tetrafluoroethylene (TFE)/propylene/vinylidene fluoride (VDF) fluorine rubber, ethylene/hexafluoropropylene (HFP) fluorine rubber, ethylene/hexafluoropropylene (HFP)/vinylidene fluoride (VdF) fluorine rubber, ethylene/hexafluoropropylene (HFP)/tetrafluoroethylene (TFE) fluorine rubber, fluorosilicone fluorine rubber and fluorophosphazene fluorine rubber. They can be used alone or can be used in arbitrary combinations, as long as the effects of the present invention are not lost. Among them, a vinylidene fluoride fluorine rubber and a tetrafluoroethylene/propylene fluorine rubber are preferable.

The vinylidene fluoride fluorine rubber means a fluorine-containing elastomeric copolymer comprising 45 to 85 mol % of vinylidene fluoride and 55 to 15 mol % of at least one other monomer copolymerizable with vinylidene fluoride. It is preferably referred to fluorine-containing copolymer comprising 50 to 80 mol % of vinylidene fluoride and 50 to 20 mol % of at least one monomer copolymerizable with vinylidene fluoride.

Examples of the at least one other monomer copolymerizable with vinylidene fluoride include, for example, fluorine-containing monomers such as tetrafluoroethylene (TFE), chlorotrifluoroethylene (CTFE), trifluoroethylene, hexafluoropropylene (HFP), trifluoropropylene, tetrafluoropropylene, pentafluoropropylene, trifluorobutene, tetrafluoroisobutene, perfluoro(alkyl vinyl ether) (PAVE), vinyl fluoride, and the like, and fluorine-free monomers such as ethylene, propylene, and alkyl vinyl ether. They can be used alone or in arbitrarily combinations. Among them, tetrafluoroethylene, hexafluoropropylene, and perfluoro (alkyl vinyl ether) are preferable.

In this case, examples of the perfluoro(alkyl vinyl ether) include, for example, perfluoro(methylvinyl ether), perfluoro(propylvinyl ether), and the like. They can be used alone or in arbitrary combinations, as long as the effects of the present invention are not lost.

Examples of the vinylidene fluoride fluorine rubber include a VDF-HFP rubber, a VDF-HFP-TFE rubber, a VDF-CTFE rubber, a VDF-CTFE-TFE rubber, and the like.

The tetrafluoroethylene/propylene fluorine rubber means a fluorine-containing elastomer copolymer comprising 45 to 70 mol % of tetrafluoroethylene, 55 to 30 mol % of propylene, and 0 to 5 mol % of a monomer providing a cross-linking site.

Examples of the monomer providing a cross-linking site include, for example, iodine-containing monomers such as perfluoro(6,6-dihydro-6-iodo-3-oxa-1-hexene) and perfluoro(5-iodo-3-oxa-1-pentene) described in JP 05-63482 B and JP 07-316234 A, bromine-containing monomers described in JP 04-505341 A, cyano group-containing monomers, carboxyl group-containing monomers and alkoxycarbonyl group-containing monomers described in JP 04-505345 A and JP 05-500070 A.

Examples of the perfluoro fluorine rubber include a perfluoro rubber containing TFE, for example, a fluorine-containing elastomer copolymer consisting of TFE/perfluoro(alkyl vinyl ether) (PAVE)/a monomer providing a cross-linking site. The composition is preferably 45 to 90/10 to 50/0 to 5 (mol %), more preferably, 45 to 80/20 to 50/0 to 5, further preferably, 53 to 70/30 to 45/0 to 2. If the composition is out of this range, property as a rubber elastomer is tend to be lost and become property close to a resin property.

In this case, examples of the PAVE include, for example, perfluoro(methylvinyl ether) (PMVE), perfluoro(propylvinyl ether) (PPVE), and the like. They can be used alone or in arbitrary combinations, as long as the effects of the present invention are not lost.

Examples of the monomer providing a cross-linking site include, for example, an iodine-containing monomer of the following formula:

$$CX_2=CX-R_fCHRI$$

wherein X is H, F or $CH_3$, $R_f$ is a fluoroalkylene group, a perfluoroalkylene group, a fluoropolyoxyalkylene group or a perfluoropolyoxyalkylene group, and R is H or $CH_3$, and a monomer of the following formula:

$$CF_2=CFO(CF_2CF(CF_3))_m-O-(CF_2)_n-Y$$

wherein m is an integer of 0-5, n is an integer of 1-3, Y is a nitrile group, a carboxyl group, an alkoxycarbonyl group or a bromine atom). They can be used alone or in arbitrary combinations, as long as the effects of the present invention are not lost. The iodine atom, the nitrile group, the carboxyl group, the alkoxycarbonyl group, and the bromine atom function as the cross-linking site.

Specific examples of the perfluoro fluorine rubber include a fluorine rubber and the like described in WO 97/24381, JP 61-57324 B, JP 04-81608 B, and JP 05-13961 B.

Examples of the other fluorine-containing polymer include homopolymer such as PVDF (polyvinylidene fluoride), PVF (polyvinyl fluoride).

The reactive compatibilizing agent of the present invention can exert its function simply by mixing the reactive compatibilizing agent containing the compound of the present invention with the compound reactive with a nitrileoxide group and the fluorine containing compound in a step of mixing the compound reactive with a nitrileoxide group and the fluorine containing compound under an atmosphere pressure in a mixing equipment (a kneader, a brabender, an extruder, etc.). In this mixing step, the compound of the present invention click-reacts with a reactive site of the compound reactive with a nitrileoxide group, thereby a fluorine-containing group can be introduced to the compound reactive with a nitrileoxide group. This introduced fluorine-containing group has an affinity for the fluorine-containing compound, thereby enabling compatibilization (complexation) of the both compounds.

The above mixing step is usually carried out at a temperature at which the compound reactive with a nitrileoxide group and the fluorine-containing compound melts, for example, about 150-250° C. For example, when NBR as the compound reactive with a nitrileoxide group is used, and PVDF as the fluorine-containing compound is used, the step is carried out at about 170° C. or more, for example, about 180-210° C. Since the compound of the present invention has a high thermal stability, such treatment at the high temperature can be carried out.

The above mixing step can be carried out usually without a solvent, additives, etc. However, the solvent or additives may be added depending on a purpose, for example in order to accelerate the reaction. Those skilled in the art can select the solvent and the additives depending on a purpose.

Examples of a conventional general compatibilizing agent are a block polymer and a graft polymer which have both backbones of two components to be complexed. The compound of the present invention is advantageous in that the preparation is easy in comparison with the conventional polymer. In addition, the reactive compatibilizing agent of the present invention has an advantage in that it can compatibilize components to be compatibilized simply by mixing the reactive compatibilizing agent with the mixture of the components.

In addition, the present invention provides a composite of two or more compounds treated with the reactive compatibilizing agent of the present invention.

In one embodiment, the composition of the present invention is a fiber treatment agent.

The fiber treatment agent of the present invention contains at least one compound (I) of the present invention, and can improve water-repellency and oil-repellency of a fiber having a group reactive with a nitrileoxide group, for example, an acrylate fiber.

The fiber treatment agent of the present invention can be suitably used for any fiber as long as it has the group reactive with a nitrileoxide group.

Examples of the fiber include an acrylate fiber, or a polyester fiber or a polyvinyl alcohol fiber obtained by copolymerizing a monomer having a nitrile group in its side chain. In addition, even a fiber having no group reactive with a nitrileoxide group become to be able to be treated with the fiber treatment agent of the present invention by introducing the group reactive with a nitrileoxide group thereto. For example, a polyester fiber or a polyvinyl alcohol fiber obtained by copolymerizing a monomer having a hydroxyl group or an amino group in its side chain become to be able to be treated with the fiber treatment agent of the present invention by dehydration-condensation with a carbonic acid or sulfonic acid compound reactive with a nitrileoxide group.

The fiber treatment agent of the present invention may contain, additives, for example, an emulsifying agent (polyethylene glycol-based, cationic, ammonium, nonionic, anionic), an antifoaming agent, a wetting agent, a paraffin hydrocarbon, and the like in addition to compound (I) of the present invention.

The fiber treatment agent of the present invention may be diluted with a solvent before being applied to the fiber. Examples of the solvent include, for example, an aliphatic perfluorohydrocarbon having 5-12 carbon atoms (for example, perfluorohexane, perfluoromethylcyclohexane and perfluoro-1,3-dimethylcyclohexane); an aromatic polyfluorohydrocarbon (for example, bis(trifluoromethyl)benzene); an aliphatic polyfluorohydrocarbon; a hydrofluoroether (HFE) (for example, an alkyl perfluoroalkyl ether such as perfluoropropyl methyl ether ($C_3F_7OCH_3$), perfluorobutyl methyl ether ($C_4F_9OCH_3$), perfluorobutyl ethyl ether ($C_4F_9OC_2H_5$), and perfluorohexyl methyl ether ($C_2F_5CF$ ($OCH_3$)$C_3F$) (the perfluoroalkyl group and the alkyl group may be liner or branched)), other fluorine solvents, hydrocarbon solvents such as a mineral oil, alcohol, MIBK (methyl isobutyl ketone), glycol-based solvents (ethylene glycol, propylene glycol etc.), and the like.

A method for applying the fiber treatment agent of the present invention to the fiber is not particularly limited as long as it can attach the desired amount of the agent of the fiber to be treated, and various methods can be used. the fiber treatment method includes, be a continuous method or a batch method.

As the continuous method, first, the fiber treatment agent is diluted with a solvent to prepare a treating liquid. Then, an object to be treated is continuously supplied to an impregnation apparatus filled with the treating liquid to impregnate the object to be treated with the treating liquid, and then unnecessary treating liquid is removed. The impregnation apparatus is not particularly limited, and is preferably a padder impregnation apparatus, a kiss roller impregnation apparatus, a gravure coater impregnation apparatus, a spray impregnation apparatus, a foam impregnation apparatus, a coating impregnation apparatus or the like, particularly preferably a padder impregnation apparatus. Then, an operation of removing the solvent remaining in the object is carried out by using a dryer. The dryer is not particularly limited, and is preferably an expansion dryer such as a tenter or a hot flue. This continuous method is employed preferably in a case where the object to be treated is cloth such as woven cloth.

The batch method comprises a step of immersing the object to be treated with a treating liquid, and a step of removing the solvent remaining in the treated object. The batch method is employed preferably in a case where the object to be treated is not cloth, such as a case where it is bulk fiber, top, sliver, hank, tow or thread, or in a case where it is not suitable for the continuous method such as a case where it is knitted fabric. In the immersion step, it is preferred to use, for example, a cotton dyeing machine, a cheese dyeing machine, a jet dyeing machine, an industrial washing machine or a beam dyeing machine. In operation of removing the solvent, it is preferred to use a hot air dryer such as a cheese dryer, a beam dryer or a tumble dryer, or a microwave dryer The treated object to which the fiber treatment agent of the present invention is attached is preferably subjected to a dry heat treatment. When the dry heat treatment is carried out, active ingredients in the fiber treatment agent of the present invention will more firmly attach to the object to be treated. The temperature for the dry heat treatment is preferably from 120 to 180° C., more preferably from 160 to 180° C. The dry heat treatment time is preferably from 10 seconds to 3 minutes, more preferably from 1 to 2 minutes. The method of the dry heat treatment is not particularly limited, and it is preferred to use a tenter in a case where the object to be treated is cloth.

In addition, the present invention provides a fiber treated with the fiber treatment agent.

The fiber treated with the fiber treatment agent of the present invention has improved water and oil repellency, weather resistance and/or thermal resistance, or the like depending on the compound of the present invention used. In addition, since the compound of the present invention is chemically bonded to the fiber by click-reaction, the above functions are less likely to deteriorate by friction, etc., and can maintain the function for a long time.

EXAMPLES

Example 1

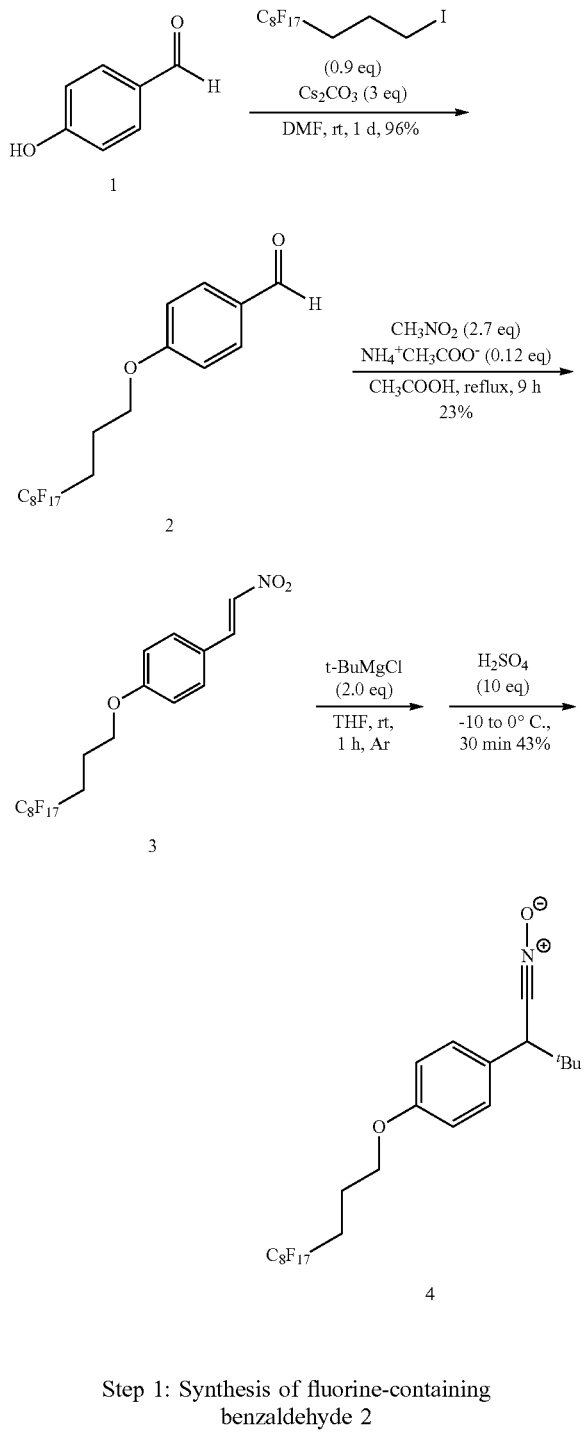

Step 1: Synthesis of fluorine-containing benzaldehyde 2

4-hydroxybenzaldehyde 1 (0.67 g, 5.5 mmol), 1-iodo-3-(perfluorooctyl)propane (2.9 g, 5.0 mmol), and cesium carbonate (5.3 g, 17 mmol) were added to anhydrous dimethylformamide (DMF) (20 mL), and reacted under an argon atmosphere at a room temperature for 20 hours. The solvent was distilled off under reduced pressure and dichloromethane was added. The mixture was extracted with water one time and with aqueous sodium hydrogen carbonate solution three times, and then dried over magnesium sulfate. The solvent was distilled off under reduced pressure to obtain a white powder 2.8 g (4.8 mmol, 96%).

Step 2: Synthesis of fluorine-containing nitrostyrene 3

Fluorine-containing benzaldehyde (22.4 g, 4.0 mmol), nitromethane (0.67 g, 11 mmol), and ammonium acetate (0.31 g, 0.48 mmol) are added to acetic acid (2 mL), and refluxed at 100° C. for 9 hours. Dichloromethane (100 mL) was added to the mixture, and the mixture was washed with water and aqueous sodium hydrogen carbonate solution, and then dried over magnesium sulfate. The mixture was filtered and the filtrate was distilled off under reduced pressure. The solid was dissolved in ethyl acetate, reprecipitated in hexane, and filtered, and then the filtrate was distilled off under reduced pressure to obtain a yellow powder (0.59 g, 0.93 mmol, 23%).

Step 3: Synthesis of fluorine-containing aliphatic nitrileoxide 4

Fluorine-containing nitrostyrene 3 (0.51 g, 0.80 mmol) was added to tetrahydrofuran (THF) (8 mL), and cooled to 0° C. under an argon atmosphere. Tert-butylmagnesium chloride (0.8 mL, 1.6 mmol) was added, and the mixture was stirred at a room temperature for 1 hour. After the mixture was cooled to −10° C., concentrated sulfuric acid (>95%, 0.42 mL, 8.0 mmol) was added, and the mixture was stirred for 30 minutes. After the mixture was extracted with water 3 times, it was dried over magnesium sulfate.

The solvent was distilled off under reduced pressure, and the mixture was purified by HPLC to obtain a white powder (0.23 g, 0.35 mmol, 43%).

Comparative Example 1

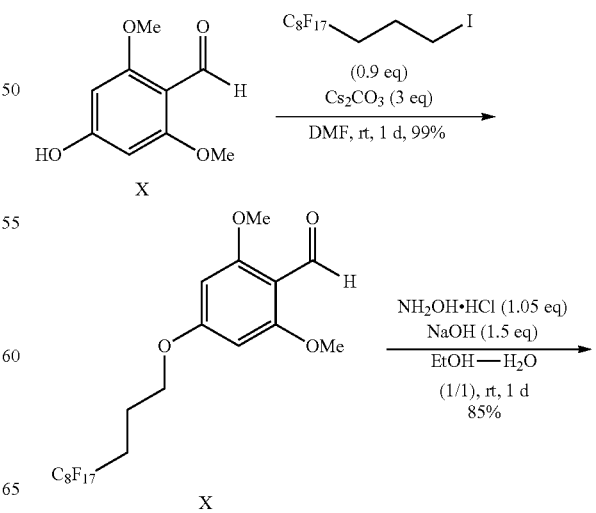

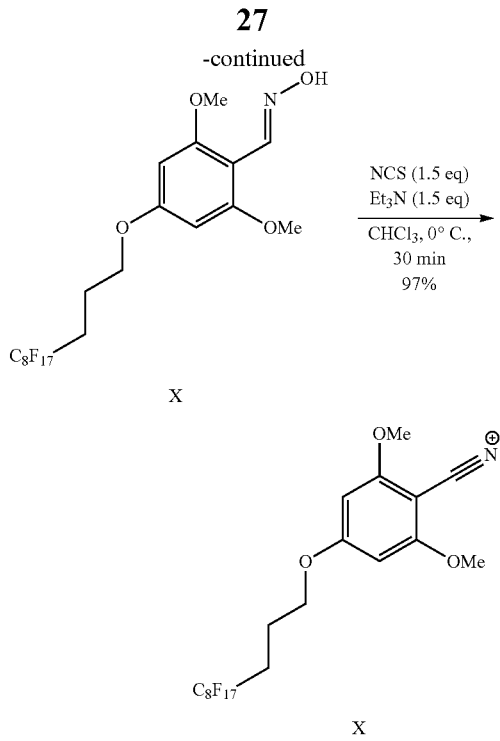

Step 1: Synthesis of fluorine-containing dimethoxybenzaldehyde 2

4-hydroxy-2,6-dimethoxybenzaldehyde (10.68 g, 3.7 mmol), 1-iodo-3-(perfluorooctyl)propane (2.0 g, 3.4 mmol) and cesium carbonate (3.7 g, 18 mmol) were added to anhydrous DMF (15 mL), and reacted under an argon atmosphere at a room temperature for 22 hours. The solvent was distilled off under reduced pressure and dichloromethane was added. The mixture was extracted with water one time and with aqueous sodium hydrogen carbonate solution three times, and then dried over magnesium sulfate. The solvent was distilled off under reduced pressure to obtain a white powder (2.0 g, 3.2 mmol, 93%).

Step 2: Synthesis of fluorine-containing dimethoxy benzaldoxime 3

While fluorine-containing dimethoxybenzaldehyde (21.2 g, 1.9 mmol) was suspended in ethanol (5 mL), a solution that hydroxylamine hydrochloride (0.15 g, 2.1 mmol) and sodium hydroxide (0.17 g, 4.3 mmol) were dissolved in water (5 mL) was added at 0° C. and stirred at a room temperature for one day. The reaction solution was filtered, and the residue was washed with pure water and chloroform and dried no obtain a white powder (1.1 g, 1.6 mmol, 85%).

Step 3: Synthesis of fluorine-containing aromatic nitrileoxide 4

While fluorine-containing dimethoxy benzaldoxime (30.14 g, 0.21 mmol) was stirred and suspended in chloroform (0.042 mL) at 0° C., triethylamine (0.040 g, 0.30 mmol), followed by N-chlorosuccinimide (NCS) (0.030 g, 0.30 mmol) were added to perform the reaction for 30 minutes. Dichloromethane was added, the mixture was extruded with water 2 times, and then dried over magnesium sulfate. The solvent was distilled off under reduced pressure to obtain a white powder (0.13 g, 0.2 mmol, 97%).

Text Example 1

Thermal Stability Test

For each of compounds obtained in Example 1 and Comparative Example 1, thermal gravimetric analysis (TGA) was performed. As a result, a temperature at which 5% weight was lost of the compound of Example 1 was 211° C., while a temperature at which 5% weight was lost of the compound of Comparative Example 1 was 180° C. It was confirmed that the compound of the present invention has superior thermal stability.

Example 2

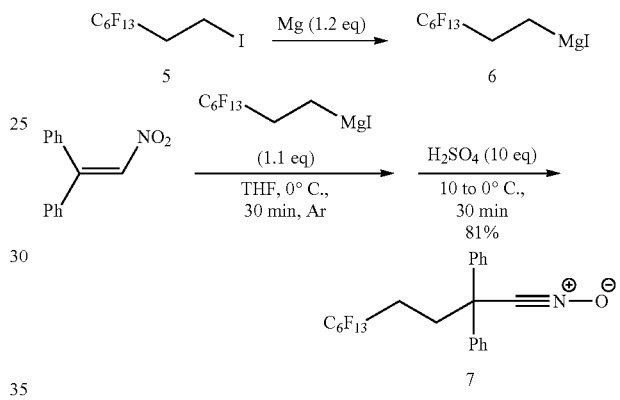

Step 1: Synthesis of fluorine-containing Grignard reagent 6

2-(perfluorohexyl)ethyl iodide (4.74 g, 10 mmol) was slowly dropped in portion into diethyl ether (25 mL) containing metallic magnesium (0.26 g, 12 mmol). The reaction solution was stirred at a room temperature for 3 hours to obtain Grignard reagent as a nucleophilic reagent (0.263 M, determined by titration with salicylaldehyde phenylhydrazone as an indicator).

Step 2: Synthesis of fluorine-containing aliphatic nitrileoxide 7

A solution of 1,1-diphenyl nitroethene (451 mg, 2.0 mmol) in dried THF (30 mL) was cooled to 0° C. under an argon atmosphere, and then the solution of Grignard reagent in diethyl ether obtained in Step 1 (8.37 mL, 2.2 mmol) was dropped in portion and stirred for 30 minutes. Then, the reaction solution was cooled to −10° C., and concentrated sulfuric acid (>95%, 1.96 g, 20 mmol) was added, and stirred at 0° C. for 30 minutes. After the reaction, the product was extracted by adding methylene chloride (50 mL) to the reaction solution, and washed with saturated sodium bicarbonate solution. The organic phase was dried over anhydrous magnesium sulfate, and the solvent was distilled off to obtain a crude product. Then, the crude product was purified by silica gel chromatography (hexane:diethyl ether=20:1) to obtain 1,1-diphenyl-3-(perfluorohexyl)propyl nitrileoxide of interest as a yellow liquid (yield 81%, 0.90 g, 1.61 mmol).

$^1$H-NMR (400 MHz, 298 K, CDCl$_3$): δ 7.42-7.29 (br, aromatic), 2.74-2.69 (m, —CF$_2$C$\underline{H}_2$—), 2.20-2.07 (m, —C$\underline{H}_2$CH$_2$—) ppm IR (KBr): 2292 (—CNO), 1636 (Ar, C=C), 1240 (C—F) cm$^{-1}$

Example 3

Solid-Phase Reaction of Natural Rubber (NR) with Fluorine-Containing Nitrileoxide 7

NR (50 mg, 0.735 mmol of repeating units) and fluorine-containing nitrileoxide 7 (C$_6$F$_{13}$C$_2$H$_4$CPh$_2$CNO, 40 mg, 0.074 mmol) (i.e., 10 mol % of nitrileoxide with respect to a C=C bond of NR) were added to a mortar, and mixed under pressure at 160° C. for 2 hours. After cooling to a room temperature, the mixture was dissolved in chloroform, precipitated in methanol, and filtered to be recovered. The recovered product was dried under vacuum to obtain a modified NR. For the obtained modified NR, the reaction rate was measured by $^1$H-NMR. In particular, depending on the progress of the reaction with nitrileoxide, proton peaks of the aromatic ring (10H, 7.3 ppm), methylene next to the perfluoro chain (2H, 2.2 ppm), and methylene further next to it (2H, 2.7 ppm) could be determined, and the reaction ratio (or conversion) was calculated based on integral value ratios between these peaks. As a result, the reaction rate was 94.7%, thus it is confirmed that the reaction was proceeded well.

Example 4

Solid-Phase Reaction of Ethylene-Propylene-Diene Rubber (EPDM) with Fluorine-Containing Nitrileoxide 7

EPDM (50 mg, 0.118 mmol of repeating units) and fluorine-containing nitrileoxide 7 (C$_6$F$_{13}$C$_2$H$_4$CPh$_2$CNO, 137.2 mg, 0.247 mmol) were added to a mortar, and mixed under a pressure at 160° C. for 2 hours. It is noted that since the contents of the diene component was 10% in EPDM, about twice nitrileoxide were used. Then, the mixture was cooled to a room temperature, and dissolved in chloroform. The product was recovered by precipitating the product in methanol. The product was dried under vacuum to obtain a modified EPDM. The reaction rate was measured by using $^1$H-NMR, as a result, it was 84.4%.

Example 5

Solid-Phase Reaction of Polyacrylonitrile (PAN) with Fluorine-Containing Nitrileoxide 7

PAN (100 mg, 1.89 mmol of repeating units) and fluorine-containing nitrileoxide 7 (523.7 mg, 0.94 mmol: corresponding to 50% of the nitrile group in PAN) were mixed under a pressure at 130° C. for 2 hours in a mortar.

After the reaction, purification was performed by extracting the mixture with acetone. The reaction rate was calculated based on the decrease of a peak of a nitrile group at 2243 cm$^{-1}$ in the FTIR (a peak at 1455 cm$^{-1}$ which can be observed before and after the reaction was referenced to). The reaction rate is 42.2%.

Example 6

Solid-Phase Reaction of Nitrile-Butadiene Rubber (NBR) with Fluorine-Containing Nitrileoxide 7

NBR (100 mg, 1.86 mmol of repeating units) and fluorine-containing nitrileoxide 7 (516.6 mg, 0.93 mmol) were mixed under a pressure at 130° C. for 2 hours in a mortar. After the reaction, purification was performed by extracting the mixture with acetone. Thought there is no referenceable peak after the reaction in NBR and it was difficult to determine an accurate reaction rate from the FTIR, the progress of the reaction was confirmed because a peak derived from CF$_3$ (at around 1200 cm$^{-1}$) and a peak derived from CF$_2$ at the low wave number side (at 702 cm$^{-1}$) were observed.

Example 7

Glass Surface Treatment

A glass slide subjected to a piranha treatment (a blank sample) was dried, and immersed in chloroform. Then, a few drops of allyltrichlorosilane (about 15 μL) were added, and the reaction was allowed at a room temperature for 12 hours. The glass slide to whose surface an allyl group was introduced was washed with chloroform several times and stored in methanol.

The glass slide to whose surface an allyl group was introduced (an allyl treated glass) was dried, and nitrileoxide 7 containing a fluorine chain (C$_E$F$_{13}$C$_2$H$_4$CPh$_2$CNO, 70 mg, 0.126 mmol) was applied thereon. The reaction was allowed on a hot plate at 70° C. for 6 hours to obtain a nitrileoxide treated glass. After the reaction, it was washed with acetone several times. The contact angle of the surface after the reaction was measured. The result is shown in the following table.

TABLE 1

| Glass sample | Contact angle (water, degree) | Contact angle (CH$_2$I$_2$, degree) | Surface energy (mJ/m$^2$) | Critical surface energy (mJ/m$^2$) |
| --- | --- | --- | --- | --- |
| blank | 41.8 | 39.0 | 62.7 | — |
| allyl treated | 59.0 | 37.3 | 53.5 | 34.8 |
| nitrileoxide treated | 95.8 | 69.7 | 25.6 | 20.7 |

The water contact angle of the glass after the piranha treatment was 41.8°, the water contact angle of the glass into which the allyl group was introduced was 59°, and the contact angles of the samples A and B into which the fluoro chain was introduced were not less than 95°. Additionally, in view of the contact angle for CH$_2$I$_2$, it was confirmed that the contact angle for an organic solvent was also improved in addition to water repellency. From these results, it was confirmed that the surface free energy was lowered and the reaction was proceeded.

Example 8

Rubber Surface Treatment

Nitrileoxide 7 containing a fluoro chain (C$_6$F$_{13}$C$_2$H$_4$CPh$_2$CNO, 30 mg) was applied to cross-linked NR film of about 15 mm×15 mm, and heated on a hot plate at 70° C. for 12 hours. After reaction, it was washed several time to remove an unreacted nitrileoxide. After the washing, the cross-liked NR film was dried.

A water contact angle of the surface of the obtained cross-linked NR film were measured. As the result, the contact angles was 86° for the unreacted NR film, and it is 92° for the NR film surface-treated with the nitrileoxide having a fluoro chain, thus it was confirmed that the reaction was proceeded.

INDUSTRIAL APPLICABILITY

The compound of the present invention can be suitably used in various applications, for example, as a surface treatment agent, a modifying agent, a filler modifier, a fiber treatment agent, a compatibilizing agent and a modifier of a rubber having a low-temperature properties.

The invention claimed is:

1. A compound of the formula (I):

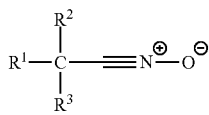

wherein
$R^1$ represents a fluoroalkyl group or a group substituted by one or more fluoroalkyl groups;
$R^2$ and $R^3$ represent each independently a hydrogen atom or a hydrocarbon group; and
a carbon atom of $R^1$ is attached to a carbon atom to which a nitrile oxide is attached, and when one or both of $R^2$ and $R^3$ is represented by a hydrocarbon group, a carbon atom of the hydrocarbon group is attached to a carbon atom to which a nitrile oxide group is attached.

2. The compound according to claim 1 wherein at least one of $R^1$, $R^2$ and $R^3$ are a perfluoroalkyl group or comprise one or more perfluoroalkyl groups.

3. The compound according to claim 1 wherein $R^1$ represents a perfluoroalkyl group, or an alkyl group substituted by one or more perfluoroalkyl groups.

4. The compound according to claim 1 which meets one or more of the following items (b)-(c);
(b) $R^2$ is an aryl group, a tert-alkyl group or a sec-alkyl group which may be substituted by one or more substituents; and
(c) $R^3$ is an aryl group, a tert-alkyl group or a sec-alkyl group which may be substituted by one or more substituents.

5. The compound according to claim 1 wherein at least one of $R^2$ and $R^3$ are an aryl group, a tert-alkyl group or a sec-alkyl group which may be substituted by one or more substituents.

6. The compound according to claim 1 wherein
$R^1$ is a perfluoroalkyl group, or an alkyl group substituted by one or more perfluoroalkyl groups; and
$R^2$ and $R^3$ are a phenyl group which may be substituted by one or more substituents.

7. The compound according to claim 1 wherein
at least one of $R^2$ and $R^3$ are a perfluoroalkyl group or an alkyl group which is substituted by one or more perfluoroalkyl groups.

8. The compound according to claim 2 wherein the perfluoroalkyl group is —$C_mF_{2m+1}$ wherein m represents an integer of 1-16.

9. A process for preparing the compound of the formula (I) described in claim 1 comprising the following steps:
(i) reacting a compound of the formula (II):

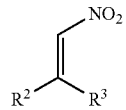

wherein: $R^2$ and $R^3$ are as defined in claim 1 with a compound of the formula (III):

wherein:
$R^1$ is as defined in claim 1;
L represents $MX_t$;
M represents Li, Zn, Na, K, Al, Cu, B, Si, Ti, Cr, Fe, Ni, Pd, Pt, Rh, Ru, Ir, Mg or Sm;
X represents a halogen atom or an alkoxy group; and
t represents an integer of 0-6; and then,
(ii) dehydrating.

10. A composition applied to a material containing a group reactive with a nitrileoxide group which comprises one or more compounds according to claim 1.

11. The composition according to claim 10 which is a surface treatment agent.

12. The composition according to claim 10 which is a modifying agent.

13. An article comprising a base material and a layer which is formed from the surface treatment agent according to claim 11 on the surface of the base material.

14. A modified polymer material treated with the modifying agent according to claim 12.

* * * * *